US012023116B2

(12) United States Patent
Overmyer et al.

(10) Patent No.: US 12,023,116 B2
(45) Date of Patent: Jul. 2, 2024

(54) DYNAMIC TROCAR POSITIONING FOR ROBOTIC SURGICAL SYSTEM

(71) Applicant: Cilag GmbH International, Zug (CH)

(72) Inventors: Mark D. Overmyer, Cincinnati, OH (US); Christopher A. Denzinger, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 370 days.

(21) Appl. No.: 17/128,792

(22) Filed: Dec. 21, 2020

(65) Prior Publication Data

US 2022/0192767 A1  Jun. 23, 2022

(51) Int. Cl.
  *B25J 9/16* (2006.01)
  *A61B 17/34* (2006.01)
  *A61B 34/30* (2016.01)
  *A61B 34/35* (2016.01)
  *A61B 17/00* (2006.01)

(52) U.S. Cl.
  CPC .......... *A61B 34/35* (2016.02); *A61B 17/3421* (2013.01); *B25J 9/1602* (2013.01); *A61B 2017/00119* (2013.01); *A61B 2017/00477* (2013.01); *A61B 2034/302* (2016.02)

(58) Field of Classification Search
  CPC ................ A61B 34/35; A61B 17/3421; A61B 2017/00119; A61B 2017/00477; A61B 2034/302; A61B 2090/064; A61B 2090/3937; A61B 34/20; A61B 34/25; A61B 34/30; A61B 34/37; A61B 90/361; A61B 90/37; A61B 2034/2055; A61B 34/70; B25J 9/1602
  See application file for complete search history.

(56) References Cited

U.S. PATENT DOCUMENTS

| | | | |
|---|---|---|---|
| 5,792,135 | A | 8/1998 | Madhani et al. |
| 6,783,524 | B2 | 8/2004 | Anderson et al. |
| 8,479,969 | B2 | 7/2013 | Shelton, IV |
| 8,573,465 | B2 | 11/2013 | Shelton, IV |
| 8,636,686 | B2 | 1/2014 | Minnelli et al. |

(Continued)

FOREIGN PATENT DOCUMENTS

EP   3473202 A1   4/2019

OTHER PUBLICATIONS

U.S. Appl. No. 17/077,067, entitled "Surgical Instrument and Carrier Kart Supporting Ultrasonic Transducer," filed Oct. 22, 2020.

(Continued)

*Primary Examiner* — Sohana Tanju Khayer
(74) *Attorney, Agent, or Firm* — Frost Brown Todd LLP

(57) ABSTRACT

A robotic surgical system includes a robotic arm, a surgical device coupled with the robotic arm and configured to extend through a body wall of a patient, and a controller in communication with the robotic arm. The controller is configured to determine a position of the surgical device relative to the patient. The controller is also configured to acknowledge a maximum allowable metric associated with the body wall at the determined position, and determine a metric associated with the body wall at the determined position. The controller is furthermore configured to drive the robotic arm to manipulate the surgical device such that the determined metric does not exceed the maximum allowable metric.

20 Claims, 12 Drawing Sheets

(56) References Cited

U.S. PATENT DOCUMENTS

| | | | |
|---|---|---|---|
| 8,690,831 B2 | 4/2014 | Duke | |
| 8,783,541 B2 | 7/2014 | Shelton, IV et al. | |
| 8,800,838 B2 | 8/2014 | Shelton, IV | |
| 11,033,344 B2* | 6/2021 | Overmyer | A61B 90/37 |
| 2009/0076476 A1* | 3/2009 | Barbagli | A61B 5/283 |
| | | | 600/587 |
| 2014/0171778 A1* | 6/2014 | Tsusaka | A61B 34/30 |
| | | | 600/407 |
| 2014/0195052 A1* | 7/2014 | Tsusaka | A61B 34/77 |
| | | | 700/260 |
| 2015/0360365 A1* | 12/2015 | Fudaba | B25J 9/1679 |
| | | | 700/254 |
| 2017/0095301 A1* | 4/2017 | Brisson | B25J 9/1607 |
| 2017/0319289 A1* | 11/2017 | Neff | A61B 90/39 |
| 2018/0296289 A1 | 10/2018 | Rodriguez-Navarro et al. | |
| 2019/0000496 A1 | 1/2019 | Shelton, IV et al. | |
| 2019/0053824 A1* | 2/2019 | Scheib | A61B 90/57 |
| 2019/0105117 A1* | 4/2019 | Brisson | A61B 34/30 |
| 2019/0321115 A1* | 10/2019 | Anderson | A61B 17/3423 |
| 2020/0113636 A1* | 4/2020 | Chino | A61B 90/37 |
| 2020/0253669 A1* | 8/2020 | Diolaiti | A61B 34/20 |
| 2021/0121258 A1* | 4/2021 | Wang | B25J 13/089 |
| 2021/0290215 A1* | 9/2021 | Amanatullah | A61B 90/06 |
| 2021/0290320 A1* | 9/2021 | Mao | A61B 34/20 |
| 2021/0367984 A1* | 11/2021 | Rajamani | G06F 16/345 |
| 2021/0401521 A1* | 12/2021 | Mantri | A61B 34/25 |
| 2022/0047347 A1* | 2/2022 | Maughan | G16H 40/40 |
| 2022/0160428 A1* | 5/2022 | Murray | A61B 17/7086 |
| 2022/0192707 A1* | 6/2022 | Barakat | A61B 34/30 |

OTHER PUBLICATIONS

International Search Report and Written Opinion dated Mar. 24, 2022, for International Application No. PCT/IB2021/062024, 12 pages.

* cited by examiner

DYNAMIC TROCAR POSITIONING FOR ROBOTIC SURGICAL SYSTEM

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one camera through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery.

MIS may be performed with non-robotic or robotic systems. Conventional robotic systems, which may include robotic arms for manipulating tools based on commands from an operator, may provide many benefits of MIS while reducing demands on the surgeon. Control of such robotic systems may require control inputs from a user (e.g., surgeon or other operator) via one or more user interface devices that translate manipulations or commands from the user into control of the robotic system. For example, in response to user commands, a tool driver having one or more motors may actuate one or more degrees of freedom of a surgical tool when the surgical tool is positioned at the surgical site in the patient.

During robotic MIS, a surgeon or other operator may use a number of different surgical instruments to perform a procedure at a surgical site. Oftentimes, a surgeon may rely on use of a surgical access device in the form of a trocar to target a surgical site within a patient's body, where the trocar provides a channel through which additional surgical instruments may be introduced and removed by a surgeon. For example, a cannula of the trocar can be inserted through the patient's abdomen to provide access to the abdominal cavity, and a surgical instrument can be inserted distally through the cannula and guided into the cavity. Merely exemplary versions of trocars are disclosed in U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; and U.S. Pat. Pub. No. 2019/0000496, entitled "Method of Suturing a Trocar Path Incision," published Jan. 3, 2019, issued as U.S. Pat. No. 11,389,192 on Jul. 19, 2022. The disclosure of each of the above-cited U.S. Patents and Publications is incorporated by reference herein.

In a robotic surgical system, a trocar may be mounted to a robotic arm that may be remotely controlled by the surgeon to move the trocar. Merely exemplary versions of such robotic systems, structures for mounting a trocar to a robotic arm of the robotic system, and methods for positioning the trocar with the robotic arm are disclosed in U.S. Pub. No. 2019/0321115, entitled "Robotic Port Placement Guide and Method of Use," published Oct. 24, 2019, issued as U.S. Pat. No. 11,039,894 on Jun. 22, 2021, and U.S. Pub. No. 2019/0053824, entitled "Cannula Attachment Devices and Methods for Surgical Robotic System," published Feb. 21, 2019, issued as U.S. Pat. No. 11,076,883 on Aug. 3, 2021, the disclosures of which are incorporated by reference herein. Other examples of robotic surgical systems are disclosed in U.S. Pat. No. 6,783,524, entitled "Robotic Surgical Tool with Ultrasound Cauterizing and Cutting Instrument," issued Aug. 31, 2004; and U.S. patent application Ser. No. 17/077,067, entitled "Surgical Instrument and Carrier Kart Supporting Ultrasonic Transducer," filed Oct. 22, 2020, published as U.S. Pat. Pub. No. 2022/0125465 on Apr. 28, 2022, the disclosures of which are incorporated by reference herein.

While various kinds of robotic surgical systems and related methods have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
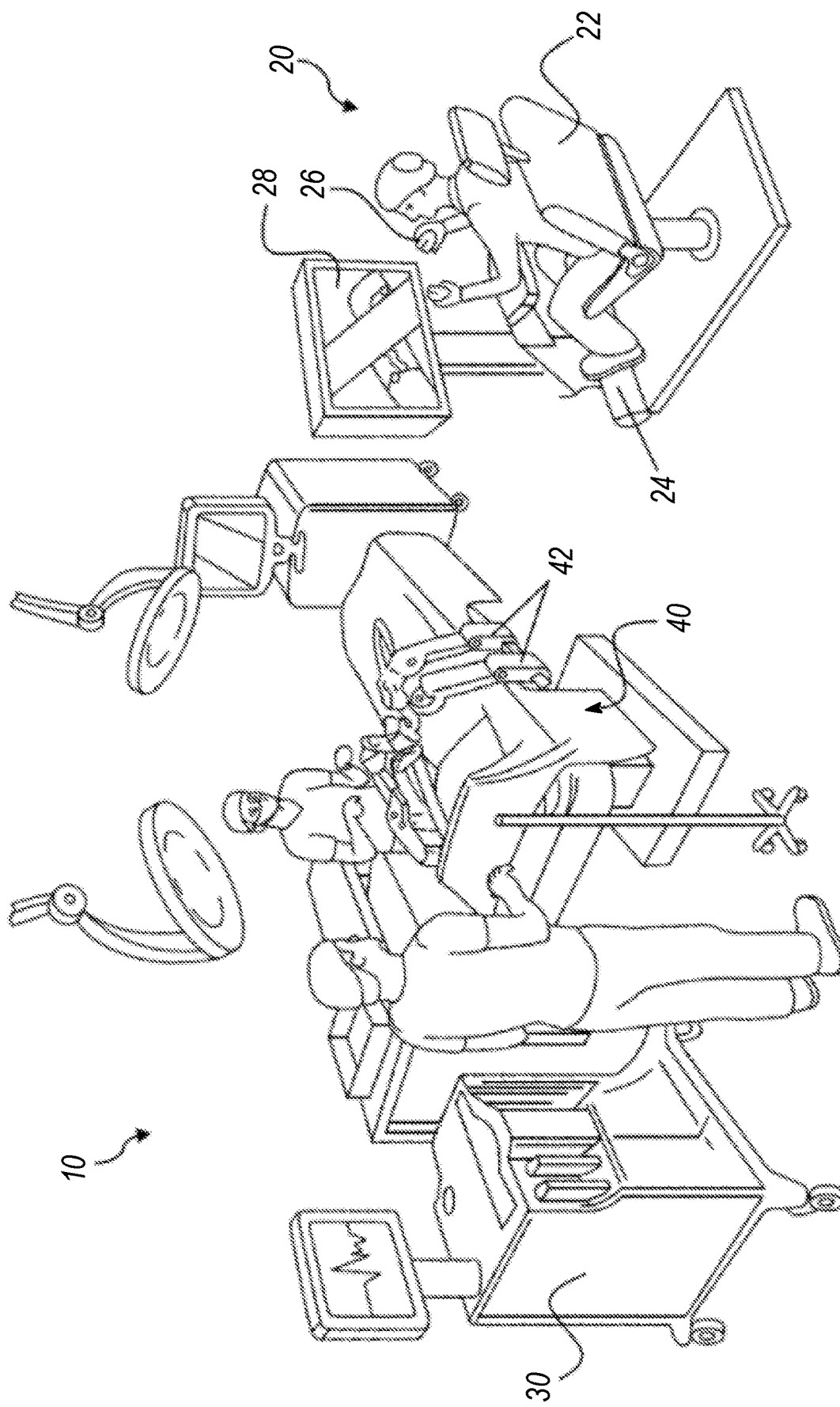
FIG. 1 depicts a schematic view of an exemplary operating room arrangement with a robotic surgical system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. EXEMPLARY ROBOTIC SURGICAL SYSTEM

FIG. 1 shows an exemplary operating room environment with a robotic surgical system (10). Robotic surgical system (10) of the present example includes a user console (20), a control tower (30), and a robotic platform (40) having one or more robotic arms (42). Though not shown in FIG. 1, surgical instruments which may include end effectors are attached to the distal ends of robotic arms (42) and are configured to be manipulated by robotic arms (42) for executing a surgical procedure. Robotic platform (40) and robotic arms (42) of the present version are shown in the form of a table-mounted (or bed-mounted) system, but it will be appreciated that robotic arms (42) may be mounted to a cart, ceiling, sidewall, or other suitable support structure in other versions.

A user, such as a surgeon or other operator, may use user console (20) to remotely manipulate robotic arms (42) and the surgical instruments supported by robotic arms (42). In some instances, user console (20) may be located in the same operating room as robotic system (10), for example as shown in FIG. 1. In other instances, user console (20) may be located in an adjacent or nearby room, or even in a different building, city, or country (each referred to as "teleoperation"). User console (20) of the present example includes a user seat (22), foot-operated controls (24), one or more handheld user interface devices (26), and a user display (28) configured to display, for example, a view of the surgical site inside a patient (e.g., captured with an endoscopic camera). In some versions, user display (28) may be in the form of a touch screen configured to receive user input via physical touch. As shown in FIG. 1, a user located in seat (22) and viewing user display (28) may manipulate foot-operated controls (24) and/or handheld user interface devices (26) to remotely control robotic arms (42) and the surgical instruments mounted to robotic arms (42) to thereby perform a surgical procedure on the patient.

During an exemplary surgical procedure, initial access to the surgical site may be performed manually, with the robotic system (10) in a stowed or withdrawn configuration to facilitate access to the surgical site. Once the initial access is completed, initial positioning and/or preparation of robotic system (10) may be performed. During the surgical procedure, a surgeon in the user console (20) may utilize foot-operated controls (24), user interface devices (26), and/or other suitable controls to manipulate various surgical instruments attached to robotic arms (42) to perform the surgery. Manual assistance may be provided at the procedure table by other personnel, who may perform supporting tasks such as retracting tissues or tool exchange involving one or more robotic arms (42).

In some versions, communication between robotic platform (40) and user console (20) may be through the control tower (30), which may translate user commands from user console (20) to robotic control commands and then transmit such commands to robotic platform (40). Additionally, control tower (30) may transmit status and feedback from robotic platform (40) back to the user console (20). Such communication between robotic platform (40), user console (20), and control tower (30) may be via wired and/or wireless connections. Control tower (30) includes a controller (not shown) that is selectively programmable and operable to perform various automated tasks based on input provided by the user and/or feedback provided by robotic platform (40).

Figure 2:
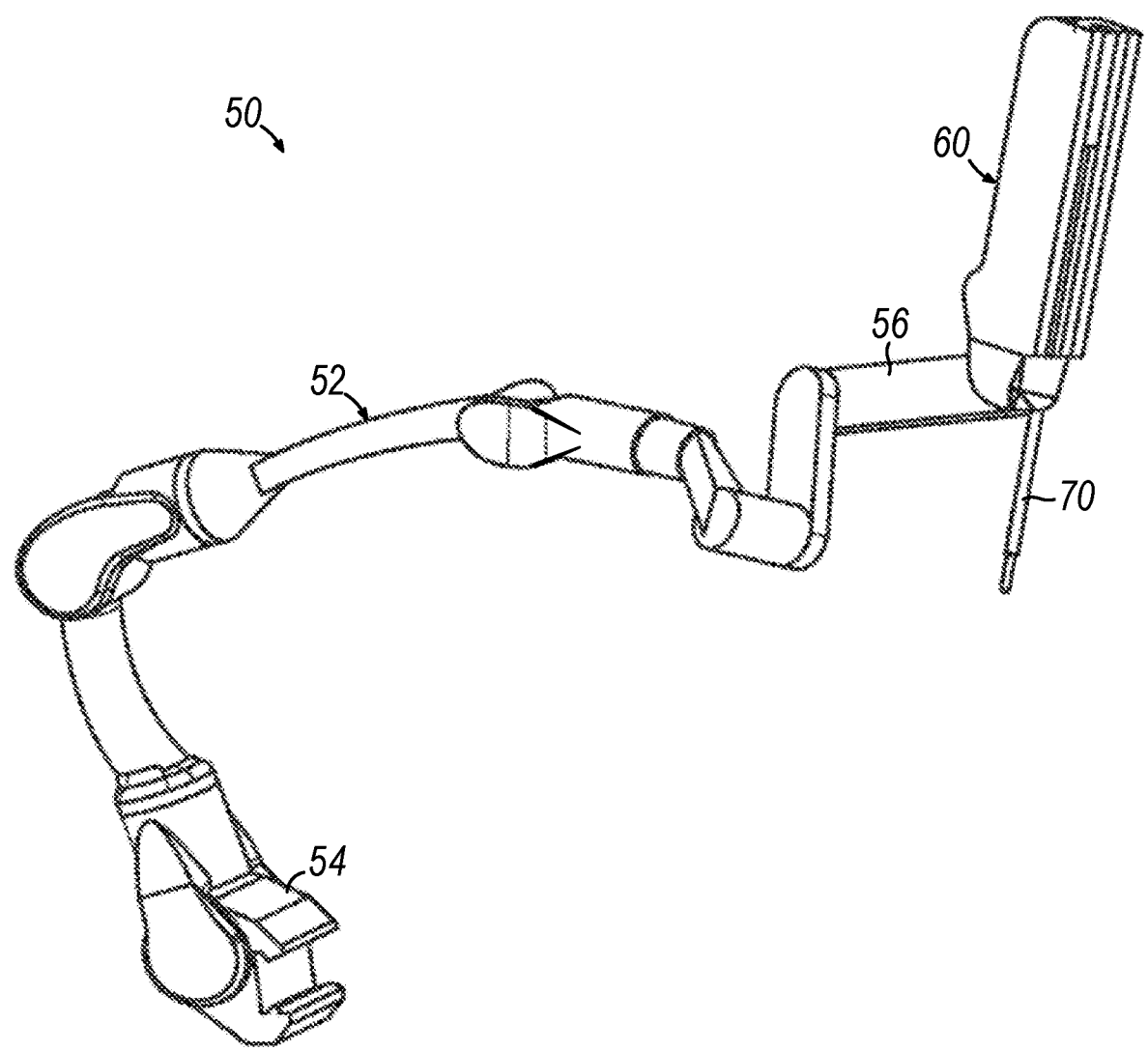
FIG. 2 depicts a perspective view of an exemplary robotic arm assembly configured for use with the robotic surgical system of FIG. 1.

FIG. 2 shows an exemplary robotic arm assembly (50) suitable for use with robotic surgical system (10) described above. Robotic arm assembly (50) of the present example includes a robotic arm (52) having a proximal arm end (54) configured to mount to a surgical table or other support structure (e.g., cart, ceiling, sidewall, etc.), and a distal arm end (56) that supports a tool driver (60). As shown in the present example, a surgical access device in the form of a trocar cannula (70) is attached to a distal end of tool driver (60). Robotic arm (52) includes a plurality of links that are independently actuatable about respective axes by respective drivers (not shown) to suitably position and orient tool driver (60) and trocar cannula (70) relative to a patient positioned on the surgical table.

Figure 4:
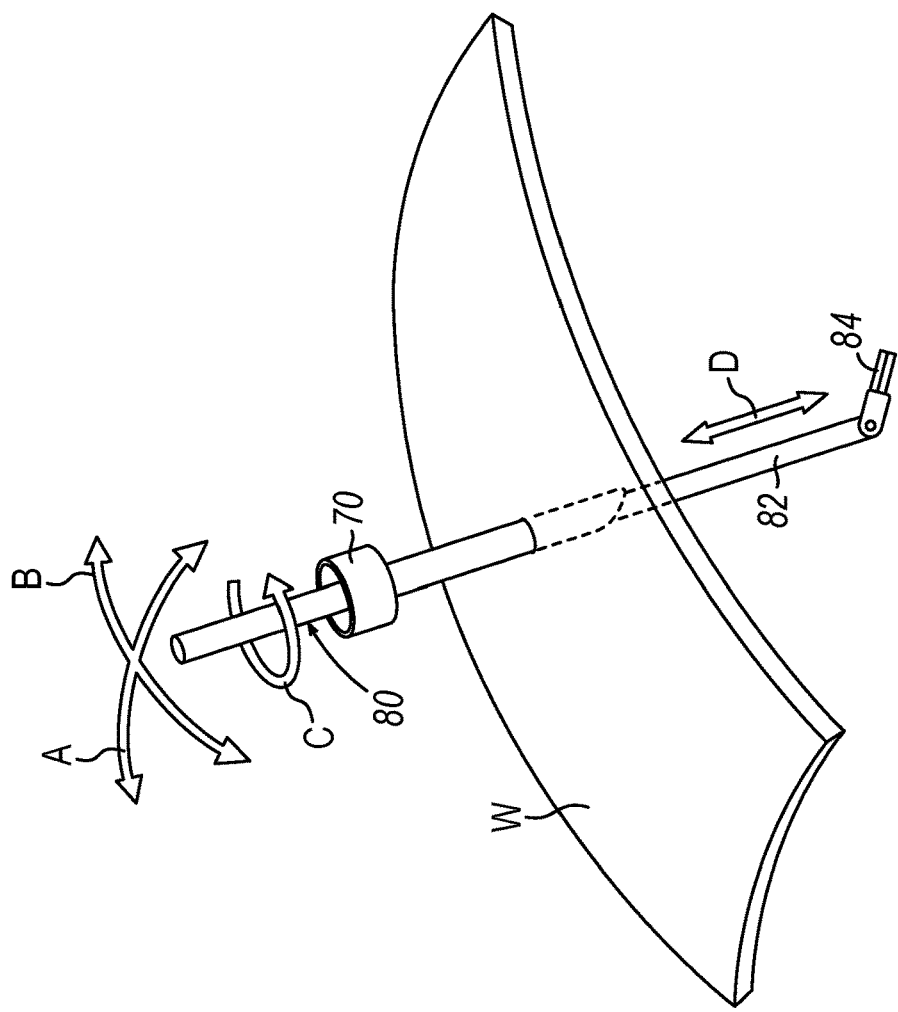
FIG. 4 depicts a schematic perspective view of the trocar cannula and a portion of the surgical tool of FIG. 3, showing exemplary degrees of freedom of the trocar and the surgical tool.
Figure 3:
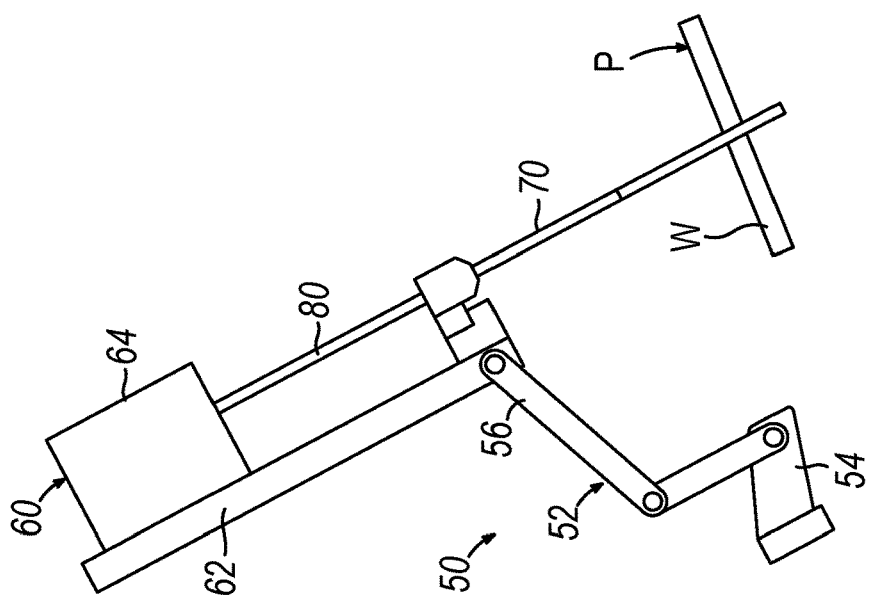
FIG. 3 depicts a schematic side view of a tool driver, a trocar cannula, and a surgical tool of the robotic arm assembly of FIG. 2.

As shown in FIGS. 3-4, tool driver (60) includes a stage (62) having a proximal end mounted to distal arm end (56) of robotic arm (52), and a distal end to which trocar cannula (70) is mounted. Tool driver (60) further includes a carriage (64) translatably coupled to stage (62), and to which a proximal portion of surgical tool (80) is mounted such that a shaft portion of surgical tool (80) is extendable distally through trocar cannula (70) and into the patient (P). Carriage (64) is actuatable relative to stage (62) to thereby move surgical tool (80) proximally and distally relative to trocar cannula (70).

As shown in FIG. 4, when trocar cannula (70) and surgical tool (80) are coupled to tool driver (60), actuation of robotic arm (52) and/or tool driver (60) relative to robotic arm (52) may provide for one or more degrees of freedom of trocar cannula (70) and surgical tool (80), including but not limited to movement of trocar cannula (70) and surgical tool (80) in a yaw or spherical roll direction (arrow A); movement of trocar cannula (70) and surgical tool (80) in a spherical pitch direction (arrow B); rotation of surgical tool (80) within and relative to trocar cannula (70) about the longitudinal axes thereof (arrow C); and/or translation of surgical tool (80) within and relative to trocar cannula (70) along the longitudinal axes thereof (arrow D).

Movement of trocar cannula (70) and surgical tool (80) in the spherical yaw and pitch directions (arrows A, B) may be controlled through actuation of at least a portion of robotic arm (52) relative to the patient (P), and may be constrained about a center of spherical rotation (i.e., tilt) relative to the patient (P), also referred to as a "remote center of motion" or simply "remote center" (RC). Rotation of surgical tool (80) within and relative to trocar cannula (70) may be controlled through one or more tool driver actuators (not shown) in carriage (64) and coupled to surgical tool (80) (e.g., directly or indirectly through a sterile barrier, etc.). Additionally, translation of surgical tool (80) within and relative to trocar cannula (70) may be controlled through one or more tool driver actuators (not shown) that translatably actuate carriage (64) relative to stage (62).

As shown in FIG. 4, surgical tool (80) of the present example includes an elongate shaft (82) and an end effector (84) at a distal end of shaft (82), which may be configured to manipulate tissue in any suitable manner, for example by grasping, clamping, cutting, sealing, and/or stapling. Carriage (64) of tool driver (60) may include one or more actuators (not shown) configured to actuate end effector (84) and/or articulate end effector (84) relative to shaft (82) to perform various tasks during a surgical procedure. It will be appreciated that at any point during a surgical procedure, surgical tool (80) may be withdrawn proximally from trocar cannula (70), decoupled from tool driver (60), and interchanged with any other suitable type of surgical tool depending on the type of surgical procedure being performed.

II. EXEMPLARY METHODS OF MANIPULATING SURGICAL DEVICE WITH ROBOTIC ARM BASED ON DYNAMIC REMOTE CENTER OF SURGICAL DEVICE

Figure 5:
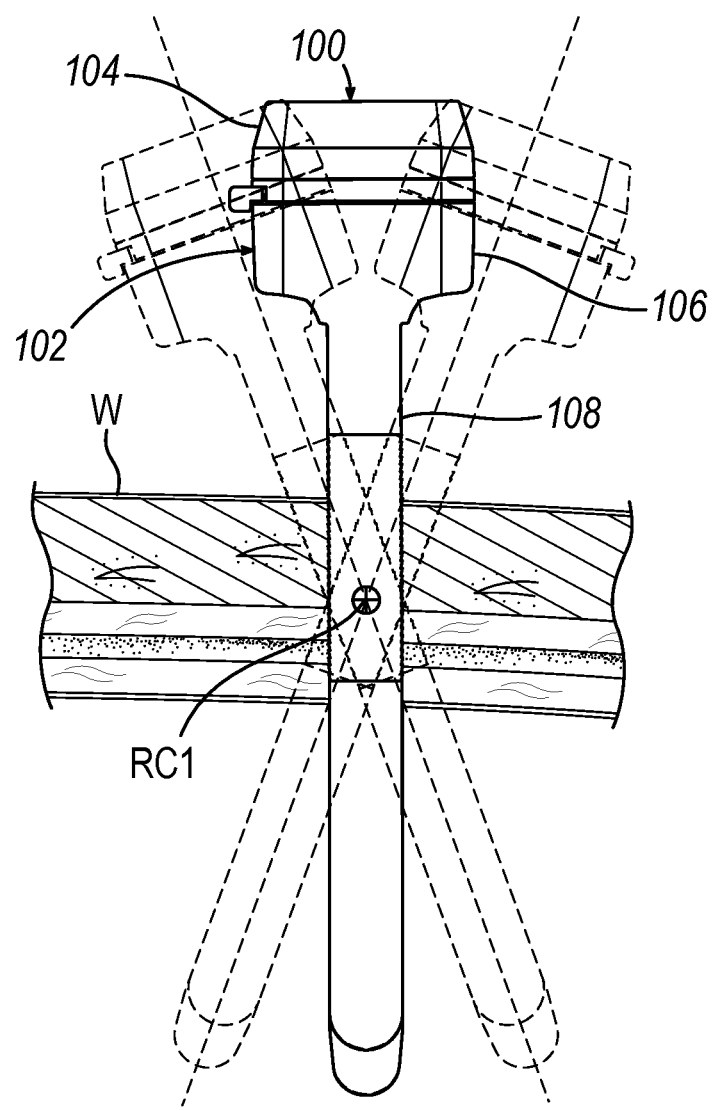
FIG. 5 depicts a schematic side cross-sectional view of a trocar cannula positioned within an abdominal wall of a patient and having a first remote center recognized by the robotic surgical system of FIG. 1, showing the first remote center located along a mid-plane of the abdominal wall such that minimal body wall compression is permitted during tilting of the trocar cannula about the first remote center, as indicated by phantom lines.

FIG. 5 shows another exemplary surgical device in the form of trocar cannula (100) positioned within an abdominal wall (W) of patient (P) and suitable for use with robotic surgical system (10). Trocar cannula (100) of the present example is configured as an assembly having a cannula member (102) and a seal housing (104). Cannula member (102) includes a bell-shaped hub (106) and an elongate cylindrical tube (108) extending distally from hub (106) and defining a working channel (not shown) configured to slidably receive a surgical instrument, such as tool (80), along a central axis thereof. Trocar cannula (100) may be further configured and operable in accordance with any of the teachings of the references incorporated by reference herein.

Similar to trocar cannula (70) described above in connection with FIG. 4, trocar cannula (100) is configured to be tilted about a remote center by robotic arm (52) relative to the abdominal wall of patient (P) in spherical rotation directions (A, B) to access a surgical site with surgical tool (80) during a surgical procedure. FIG. 5 illustrates trocar cannula (100) with a first remote center (RC1) recognized by control tower (30) of robotic surgical system (10), wherein the first remote center (RC1) is located approximately along a mid-plane of the abdominal wall (W) of patient. Accordingly, as indicated by the phantom lines in FIG. 5, trocar cannula (100) induces minimal deformation (e.g., compression) of abdominal wall (W) in lateral directions when tilted about the first remote center (RC1) by robotic arm (52) during a surgical procedure. Moreover, first remote center (RC1) may be maintained at this location throughout a surgical procedure such that trocar cannula (100) is deemed to have a "static" remote center.

Figure 6:
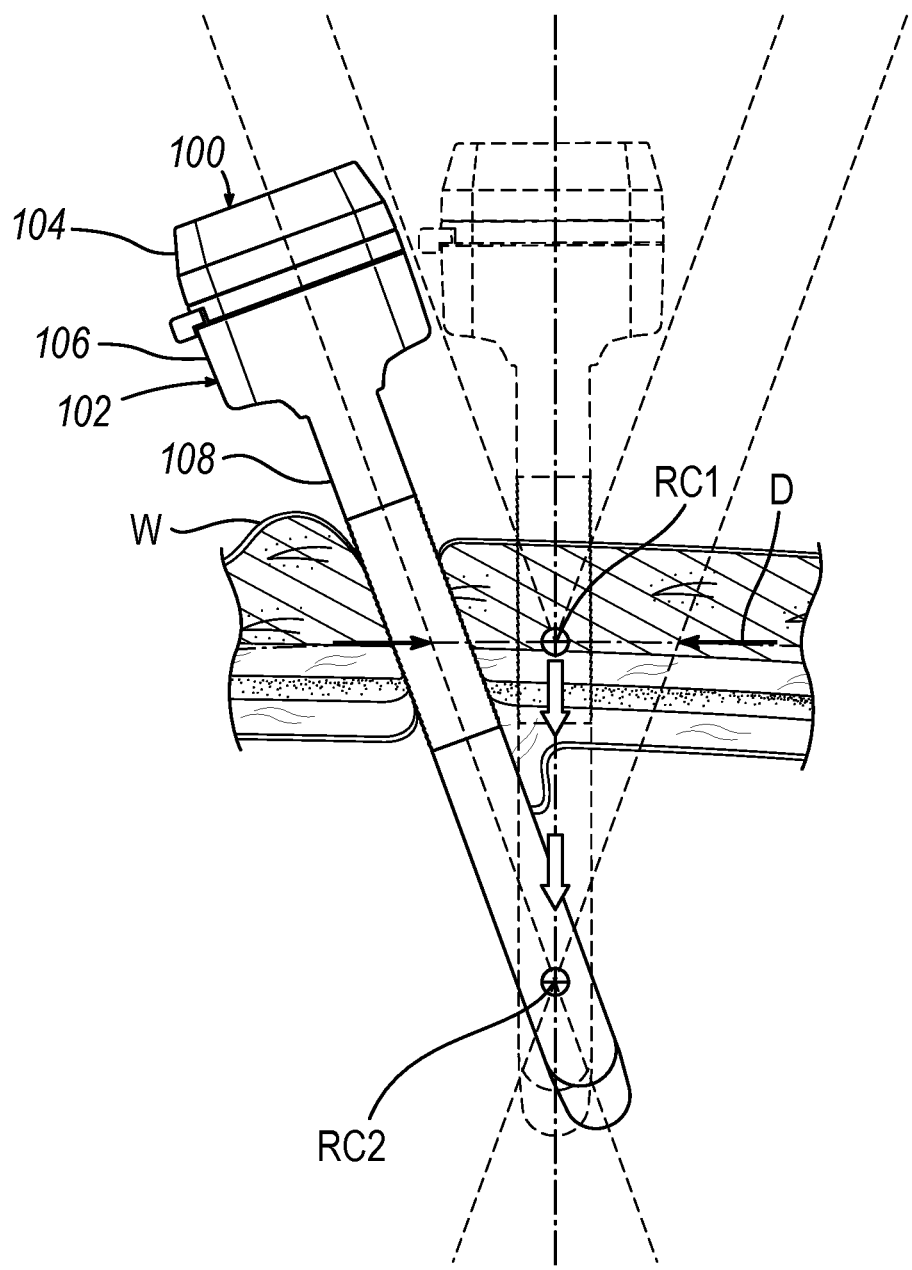
FIG. 6 depicts another schematic side cross-sectional view of the trocar cannula and abdominal wall of FIG. 5 having a second remote center recognized by the robotic surgical system of FIG. 1, showing the second remote center located distal to the first remote center of FIG. 5 such that greater body wall compression is permitted during tilting of the trocar cannula about the second remote center, as indicated by phantom lines.

In some instances, however, it may be desirable to adjust a location of the remote center of trocar cannula (100) recognized by control tower (30) in distal or proximal directions along the central axis of trocar cannula (100), to thereby adjust the point about which trocar cannula (100) is tilted in spherical directions (A, B) by robotic arm (52) during a surgical procedure. For instance, as shown in FIG. 6, control tower (30) may observe a second remote center (RC2) of trocar cannula (100) that is distal to its first remote center (RC1) shown in FIG. 5, and distal to a lower surface of abdominal wall (W). Accordingly, in the present example, control tower (30) controls robotic arm (52) to tilt trocar cannula (100) in spherical directions (A, B) about a more distal point of trocar cannula (100) as compared to the configuration shown in FIG. 5 with first remote center (RC1). Consequently, this second configuration results in greater lateral deformation of abdominal wall (W) during such tiling of trocar cannula (100). However, it also provides greater reach within the body cavity and enhanced access to the surgical site with a surgical instrument directed through trocar cannula (100), for example when an end effector of the surgical instrument is in an articulated state.

In other versions, control tower (30) may alternatively position second remote center (RC2) to yield differing effects on the lateral deformation of abdominal wall (W) caused by the tilting of trocar cannula (100) during a surgical procedure. For instance, control tower (30) may observe a second remote center (RC2) that is proximal to first remote center (RC1) and distal to, in longitudinal alignment with, or proximal to the upper surface of abdominal wall (W). Still in other versions, control tower (30) may observe a second remote center (RC2) that is laterally offset from first remote center (RC1) and in longitudinal alignment with, distal to, or proximal to first remote center (RC1).

It will be appreciated that the abdominal wall (W) of a patient (P) has a flexibility that varies from one region of the abdominal wall (W) to the next, such that different regions of the abdominal wall (W) may be able to withstand different maximum degrees of lateral deformation (e.g., compression). Upon comparison of FIGS. 5 and 6, it will also be appreciated that as the remote center of trocar cannula (100) is located further distally from the mid-plane of abdominal wall (W) to achieve enhanced reach and access with a surgical instrument as described above, the lateral deformation of abdominal wall imposed by trocar cannula (100) while being tilted in spherical directions (A, B) by robotic arm (52) will increase.

Accordingly, in order to avoid excessive deformation of and resulting trauma to the abdominal wall (W) due to lateral forces exerted on abdominal wall (W) during tilting of trocar cannula (100) with a distally positioned remote center (e.g., RC2), it may be desirable to provide control tower (30) of robotic surgical system (10) with the ability to select and dynamically adjust the location of the remote center along trocar cannula (100) during a surgical procedure, for instance depending on the region of abdominal wall (W) in which trocar cannula (100) is positioned. FIGS. 7-13 described below illustrate exemplary methods of manipulating trocar cannula (100) with robotic surgical system (10) in such a manner. It will be appreciated that these methods may be employed in connection with any of the exemplary robotic arms and trocar cannulas disclosed herein.

Figure 7:
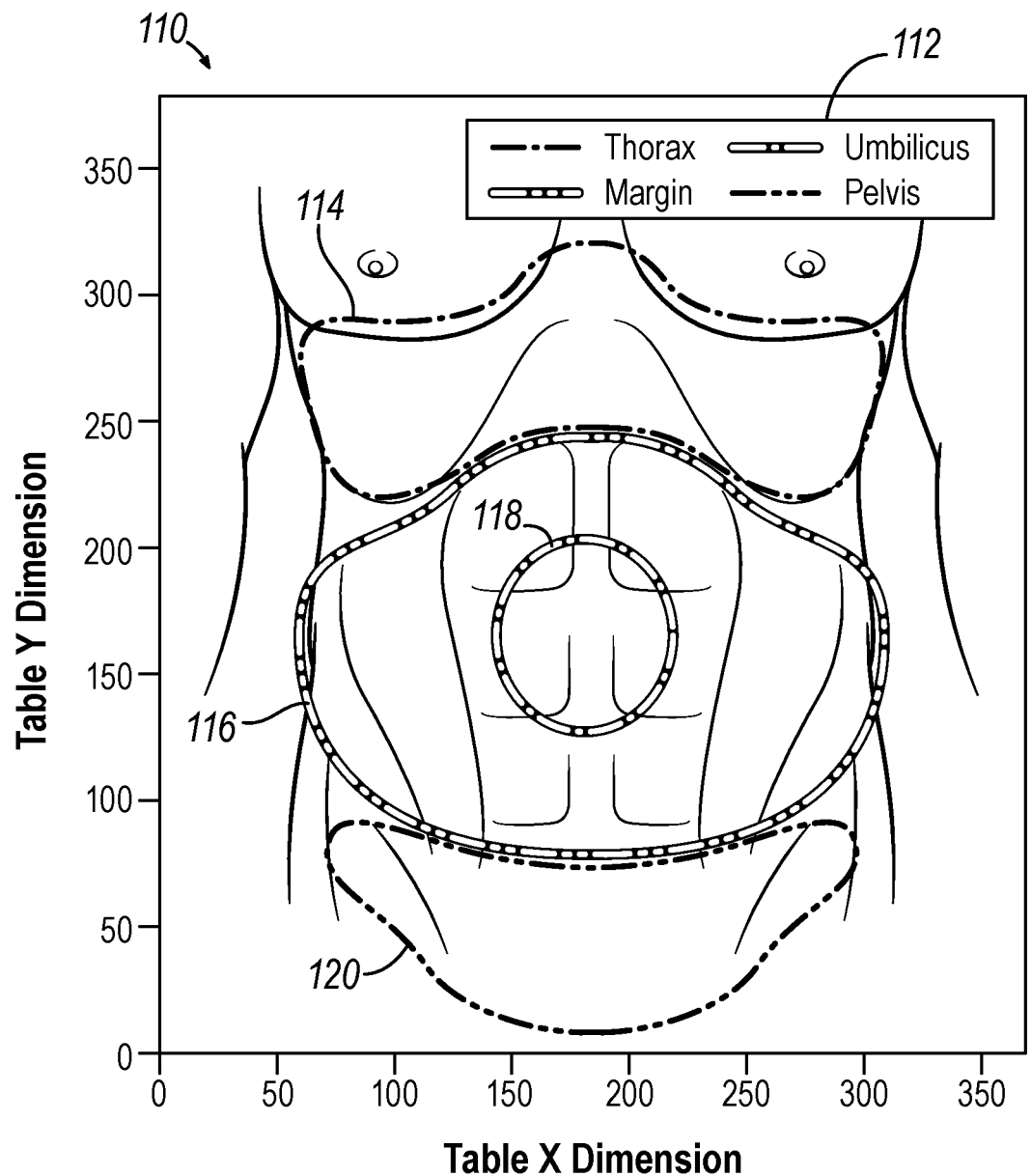
FIG. 7 depicts a schematic graphical view of an exemplary coordinate system and predefined body regions superimposed over the body of a patient.

A. Exemplary Methods of Manipulating Surgical Device Based on Predefined Maximum Body Wall Deformation Values FIG. 7 shows an exemplary graph (110) that depicts locations of various body regions of a patient (P) within a coordinate system defined by a surgical table (T) on which the patient (P) is lying supine for a surgical procedure with robotic surgical system (10). More specifically, the X-axis of graph (110) indicates distances along a width dimension of surgical table (T), and the Y-axis of the graph (110) indicates distances along a length dimension of surgical table (T). Graph (110) depicts a plurality of closed curves, each of which defines a corresponding body region of patient (P) through which abdominal wall (W) extends. In particular, as indicated by key (112) of graph (110), a first curve (114) defines the outer boundary of a thorax region of patient (P); a second curve (116) defines the outer boundary of a margin region of patient (P); a third curve (118) defines the outer boundary of an umbilicus region of patient (P) located centrally with the margin region; and a fourth curve (120) defines the outer boundary of a pelvis region of patient (P). Accordingly, curves (114, 116, 118, 120) delineate various portions of the abdomen and chest regions of patient (P).

Figure 8:
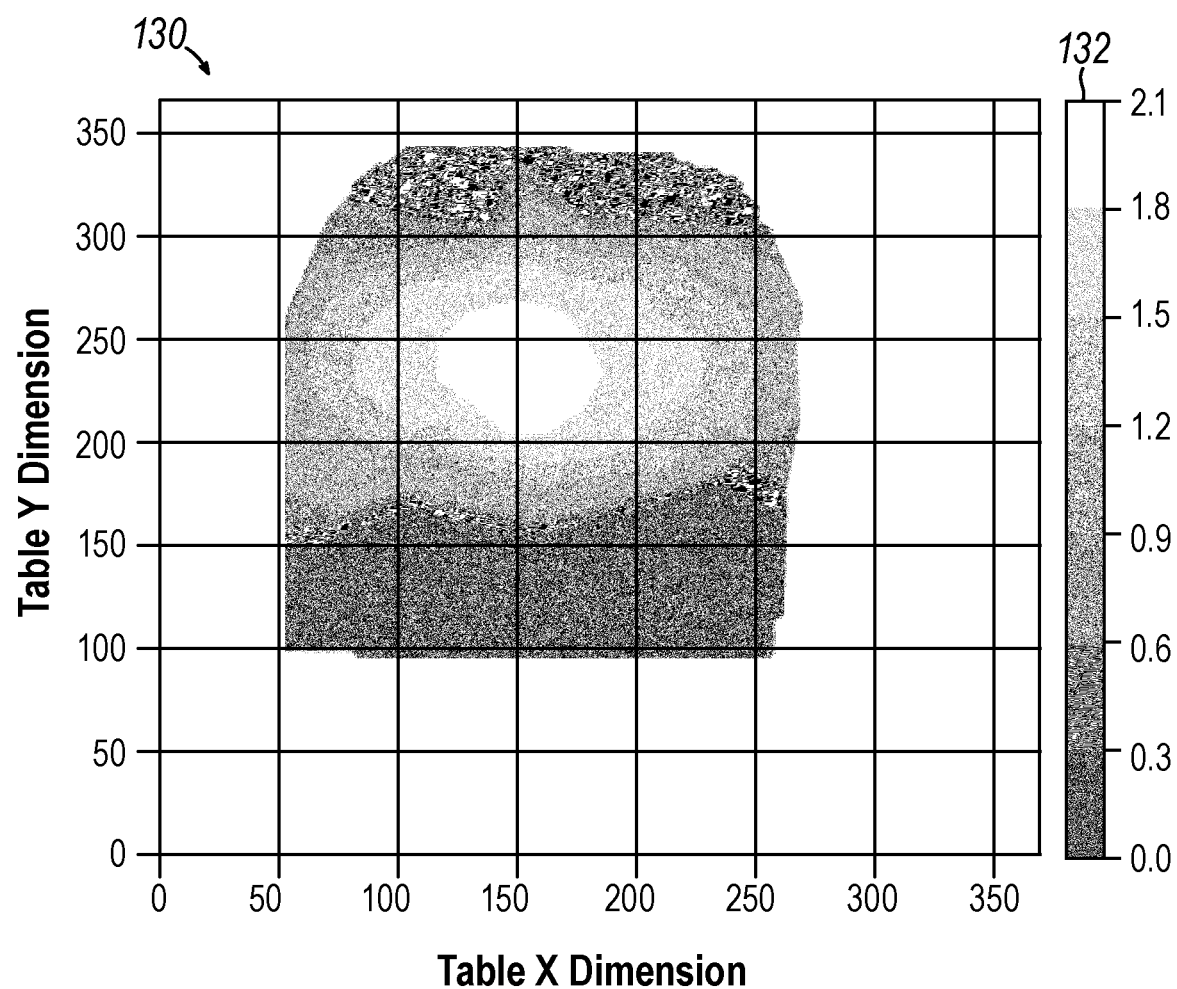
FIG. 8 depicts a graphical view showing the coordinate system of FIG. 7 and exemplary maximum allowable values of body wall compression at various locations throughout the coordinate system corresponding to the body regions of FIG. 7.

FIG. 8 shows another exemplary graph (130) having X and Y axes that correspond to width and length dimensions, respectively, of surgical table (T) on which patient (P) is positioned, similar to graph (110) described above. Graph (130) includes shading that depicts maximum allowable deformations of abdominal wall (W) of patient (P) in lateral directions by a surgical access device extending through abdominal wall (W), such as trocar cannula (100), at corresponding locations of abdominal wall (W). As indicated by key (132) of graph (130), darker shading indicates lesser maximum allowable deformation and lighter shading (including absence of shading) indicates greater maximum allowable deformation. Thus, as will be understood by graph (130) and its key (132), in combination with graph (110) and its key (112) of FIG. 7, portions of abdominal wall (W) within the umbilicus region of patient (P) indicated by third curve (118) in graph (110) have greater flexibility and thus may undergo greater maximum allowable deformation. By comparison, portions of abdominal wall (W) within the thorax and pelvis regions of patient (P), indicated by first curve (114) and fourth curve (120), respectively, have lesser flexibility and thus may undergo lesser maximum allowable deformation. As indicated by the gradient of shading in graph (130), such flexibility and corresponding maximum allowable formation may gradually decrease in directions away from the patient's umbilicus region.

As shown by FIGS. 6-8 in combination, each of the four body regions depicted in graph (110) of FIG. 7 may be constrained to a maximum allowable deformation presented in the form of a diameter (D). As shown in FIG. 6, maximum allowable deformation diameter (D) is defined by the lateral distance along the mid-plane of abdominal wall (W) between the centerline of trocar cannula (100) in each of two diametrically opposed, maximum angled states. By way of example only, locations within the umbilicus region enclosed by third curve (118) in graph (110) may be subject to a maximum allowable deformation diameter (D) of less than or equal to approximately 2.1 inches; locations within the margin region enclosed by second curve (116) in graph (110) may be subject to a maximum allowable deformation diameter (D) that varies between approximately 2.0 inches and 0.5 inches; locations within the thorax region enclosed by first curve (114) in graph (110) may be subject to a maximum allowable deformation diameter (D) of less than or equal to approximately 0.5 inches; and locations within the pelvis region enclosed by fourth curve (120) in graph (110) may be subject to a maximum allowable deformation diameter (D) of less than or equal to approximately 0.5 inches.

Control tower (30) of robotic surgical system (10) may be configured to access a database that correlates maximum allowable deformation values (or alternatively, maximum allowable force values, as described below) with body regions of the patient (P), and specifically various portions of abdominal wall (W). Such a database may be stored locally in the memory of control tower (30), or alternatively it may be stored remotely, for example on a cloud platform. In some versions, such a database may be generated based on inputs specified by a user via user console (20) before or during the surgical procedure.

Additionally, control tower (30) may determine or otherwise be instructed of the specific location of trocar cannula (100) relative to abdominal wall (W) and then identify or otherwise interpolate a maximum allowable deformation value (or alternatively, a maximum allowable force value) corresponding to that location. Such interpolation by control tower (30) may be executed via a pre-programmed interpolation function based on the one or more nearest discrete value(s) provided within the accessed database. By way of example only, such an interpolation function may be piecewise linear, piecewise cubic, C1 smooth, or curvature-minimizing. In other versions, a maximum allowable deformation value (or alternatively, a maximum allowable force value) corresponding a known location of trocar cannula (100) relative to patient (P) may be determined by control tower (30) using a variety of other suitable methods that will be readily apparent to those of ordinary skill in the art in view of the teachings herein. By way of example only, such methods may include computation of convex hull; Delaunay triangulation, Voronoi diagram, half-space intersection about a point, furthest-site Delaunay triangulation, and/or furthest-site Voronoi diagram, for example via a Quickhull algorithm.

Control tower (30) may then suitably control robotic arm (52) to manipulate trocar cannula (100) and surgical instrument (80) so as to not exceed the maximum deformation value (or alternatively, the maximum allowable force value), thereby avoiding unwanted trauma to the patient's abdominal wall (W) while taking advantage of enhanced reach and surgical site access enabled by a distally positioned remote center, as described above. In some versions, control tower (30) may be further configured to adjust the remote center of trocar cannula (100) during a surgical procedure to reduce lateral deformation of abdominal wall (W) in response to detecting that the maximum allowable deformation value has been reached or exceeded.

Figure 9:
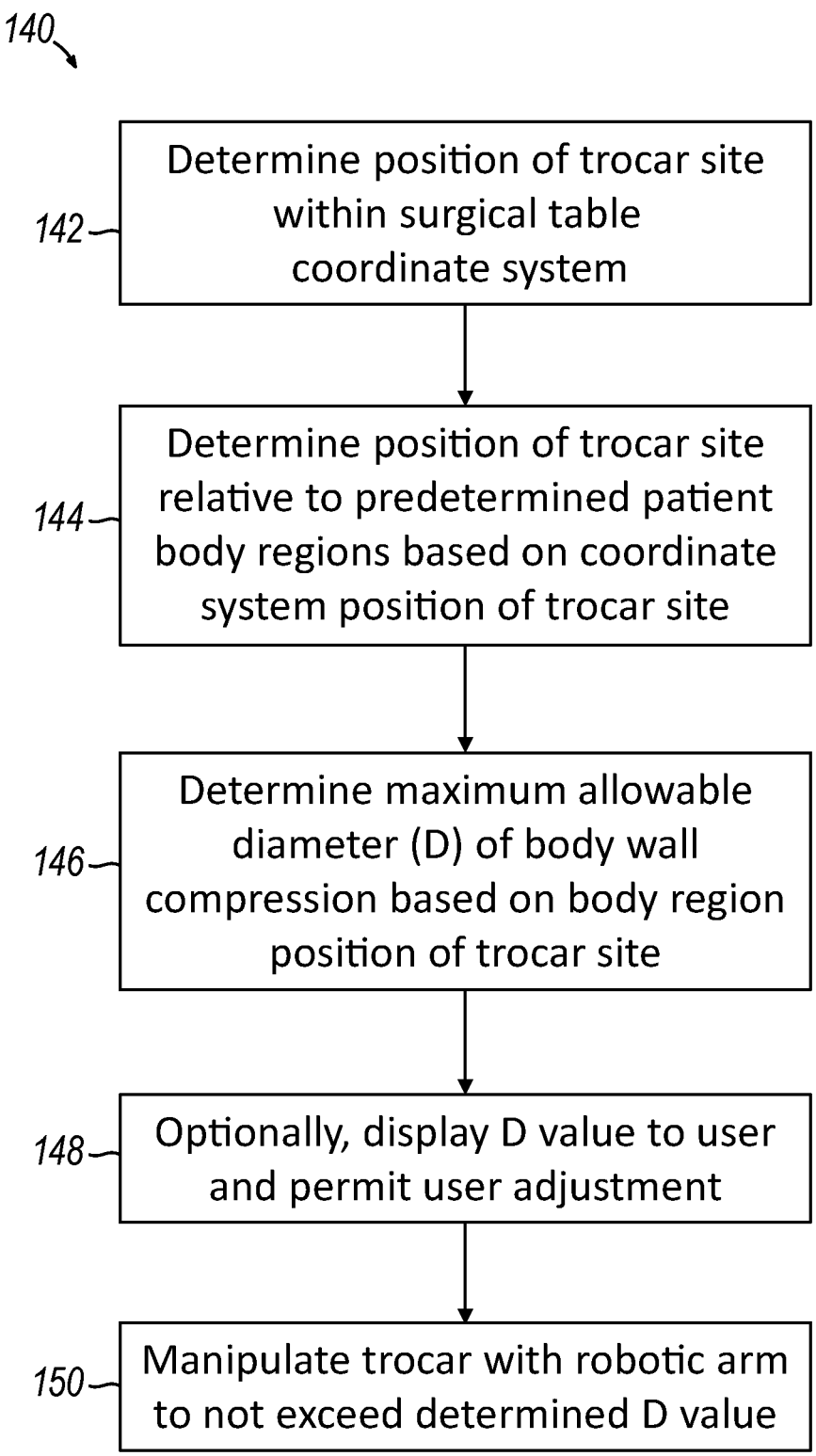
FIG. 9 depicts a diagrammatic view of an exemplary method of manipulating a surgical device relative to a patient using the robotic surgical system of FIG. 1.

FIG. 9 shows an exemplary method (140) of manipulating trocar cannula (100) with robotic arm (52) of robotic surgical system (10) in the manner summarized above. At step (142), control tower (30) determines a position of trocar cannula (100) within an X-Y coordinate system defined by surgical table (T), for example as shown and described above in connection with FIGS. 7-8, or alternatively another reference structure located in the operating room. Step (142) may be performed based on one or more cameras or other sensors (not shown) in communication with control tower (30), and/or based on manual input provided by a user via user console (20). At step (144), control tower (30) determines in which body region of patient (P) the determined coordinate system position of trocar cannula (100) is situated. Based on the determination of step (144), control tower (30) at step (146) determines a metric in the form of a maximum allowable deformation value of abdominal wall (W) that corresponds to the determined coordinate system position via the determined body region. As described above, this maximum allowable deformation value may be in the form of a maximum allowable deformation diameter (D) at the site of trocar cannula (100). Control tower (30) may perform step (146) by accessing a database that correlates body region with maximum allowable deformation. As described above, such a database may be stored locally in the memory of control tower, or alternatively it may be stored remotely, for example on a cloud platform. In some versions, steps (144) and (146) may be performed by control tower (30) as a single step by accessing a database that correlates coordinate system positions of trocar cannula (100) directly with predefined maximum allowable deformation values.

Still in other versions, control tower (30) may receive user input that specifies the maximum allowable deformation value, for example via user console (20). In all such versions in which control tower (30) either determines the maximum allowable deformation value or receives the maximum allowable deformation value via user input, it will be understood that control tower (30) "acknowledges" the maximum allowable deformation value, for example in order to perform step (150) described below.

At step (148) of method (140), control tower (30) may direct user console (20) to display to the user the maximum allowable deformation value determined in step (146), and then permit the user to adjust the value as desired. In some versions, such user adjustment of the value in step (148) may be performed via relocating one or more symbols or other visual markings displayed on user display (28) relative to a visual representation of patient (P). It will be appreciated that step (148) is merely optional and may be omitted in some versions such that control tower (30) may proceed directly from step (146) to step (150). At step (150), control tower (30) directs robotic arm (52) to manipulate trocar cannula (100) based on user inputs made via user console (20) to perform a surgical procedure on patient (P), and such that lateral deformation of abdominal wall (W) imposed by angular deflection of trocar cannula (100) about its remote center by robotic arm (52) does not exceed the maximum allowable deformation value determined in step 06. If control tower (30) determines that the actual lateral deformation of abdominal wall (W) during the surgical procedure exceeds the maximum allowable deformation value, control tower (30) may perform one or more of the following actions: (i) interrupt all motion of robotic arm (52); (ii) provide a warning message to the user via user console (20); (iii) adjust the remote center of trocar cannula (100) in a direction toward the outer proximal surface of abdominal wall (W) by a predetermined distance to thereby reduce the lateral deformation of abdominal wall (W) by trocar cannula (100); or (iv) inhibit motion of robotic arm (52) that would yield a lateral deformation of abdominal wall (W) that exceeds the maximum allowable deformation value, while still permitting motion of robotic arm (52) that would yield a lateral deformation of abdominal wall (W) that is less than or equal to the maximum allowable deformation value.

B. Exemplary Methods of Manipulating Surgical Device Based on Predefined Force Limits In some instances, it may be desirable to configure control tower (30) to regulate the manipulations of trocar cannula (100) by robotic arm (52) based on a predefined threshold force that corresponds to the location of trocar cannula (100) within abdominal wall (W) of patient (P). As described in greater detail below, FIGS. 10-13 illustrate exemplary methods that incorporate versions of this approach.

Figure 10:
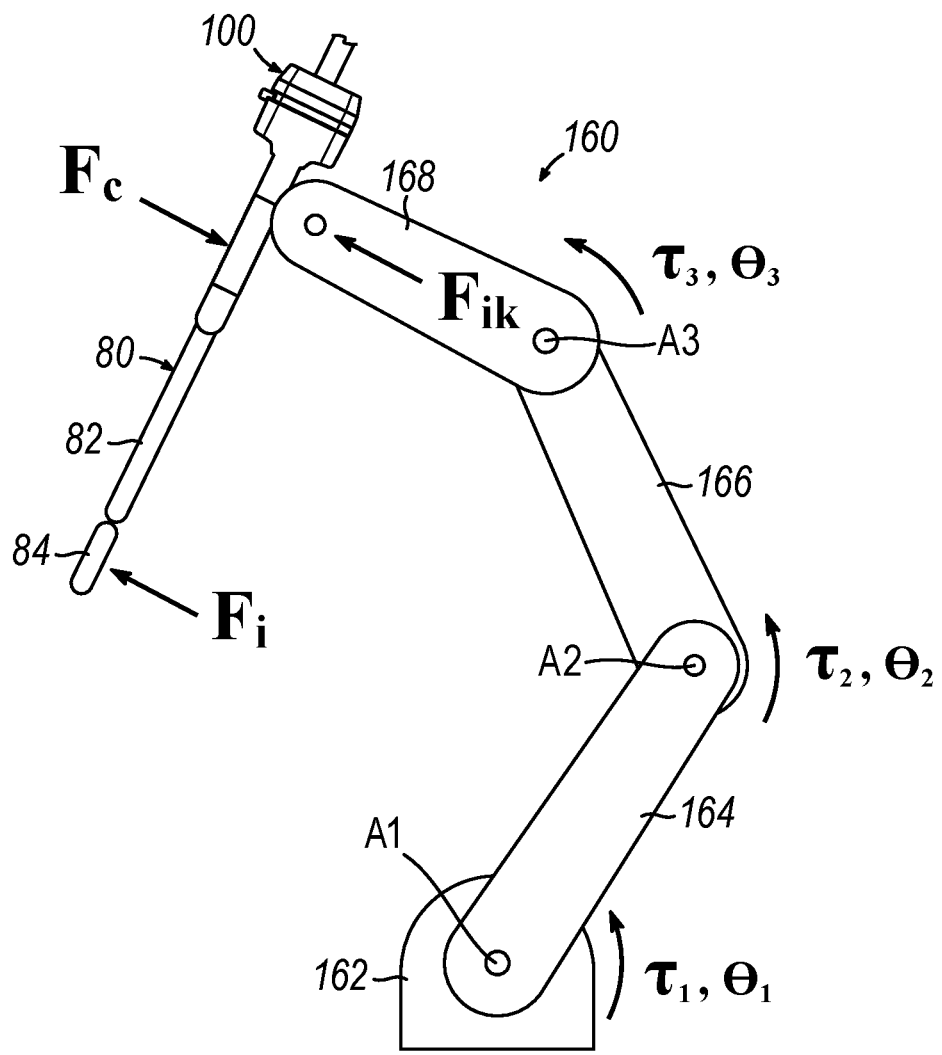
FIG. 10 depicts a schematic view of an exemplary robotic arm assembly configured for use with the robotic surgical system of FIG. 1, showing exemplary force vectors acting at various points throughout the robotic arm assembly.

FIG. 10 shows another exemplary robotic arm (160) that is similar to robotic arms (42, 52) described above and which is configured for use with robotic surgical system (10) of FIG. 1. Robotic arm (160) includes a proximal base (162) configured to amount to a support structure, such as a surgical table (T); a first link (164) pivotably coupled with base (162) about a first pivot axis (A1); a second link (166) pivotably coupled with a distal end of first link (164) about a second pivot axis (A2); and a third link (168) pivotably coupled with a distal end of second link (166) about a third pivot axis (A3). Trocar cannula (100) and surgical instrument (80) are coupled to a distal end of third link (168). Each link (164 166, 168) is configured to be pivotably driven at its proximal end about the respective pivot axis (A1, A2, A3) through a respective range of angular motion ($\theta_1$, $\theta_2$, $\theta_3$) and with a respective torque ($\tau_1$, $\tau_2$, $\tau_3$) by a respective actuator (not shown), such as a motor or linear actuator.

The torque ($\tau_1$, $\tau_2$, $\tau_3$) exerted at each pivot axis (A1, A2, A3) of robotic arm (160) may be measured by a respective torque sensor (not shown), or alternatively calculated via a force sensor measurement. Additionally, the angular position ($\theta_1$, $\theta_2$, $\theta_3$) of each link (164 166, 168) may be monitored by a respective position sensor (not shown), such as an encoder. All such sensors communicate with control tower (30) of robotic surgical system (10), such that the control tower (30) may determine an inverse kinematic force ($F_{ik}$) acting on trocar cannula (100) at the distal end of third link (168), based on the sensor signals and known mass properties of robotic arm links (164, 166, 168), and optionally also trocar cannula (100) and surgical instrument (80).

Surgical instrument (80) may be equipped with a force sensor (not shown) at its end effector (84), and such force sensor may communicate with control tower (30) so that control tower (30) may determine an instrument force ($F_i$) exerted between end effector (84) and an anatomical structure of the patient (P) during a surgical procedure. Based on the instrument force ($F_i$) and the inverse kinematic force ($F_{ik}$), control tower (30) may then determine a cannula force ($F_c$) exerted laterally between trocar cannula (100) and abdominal wall (W) through which trocar cannula (100) extends. Control tower (30) may continuously determine this cannula force ($F_c$) throughout a surgical procedure and direct robotic arm (160) appropriately so that the cannula force ($F_c$) does not exceed a predetermined threshold force, which may correspond to the specific body region at which trocar cannula (100) is located.

Figure 11:
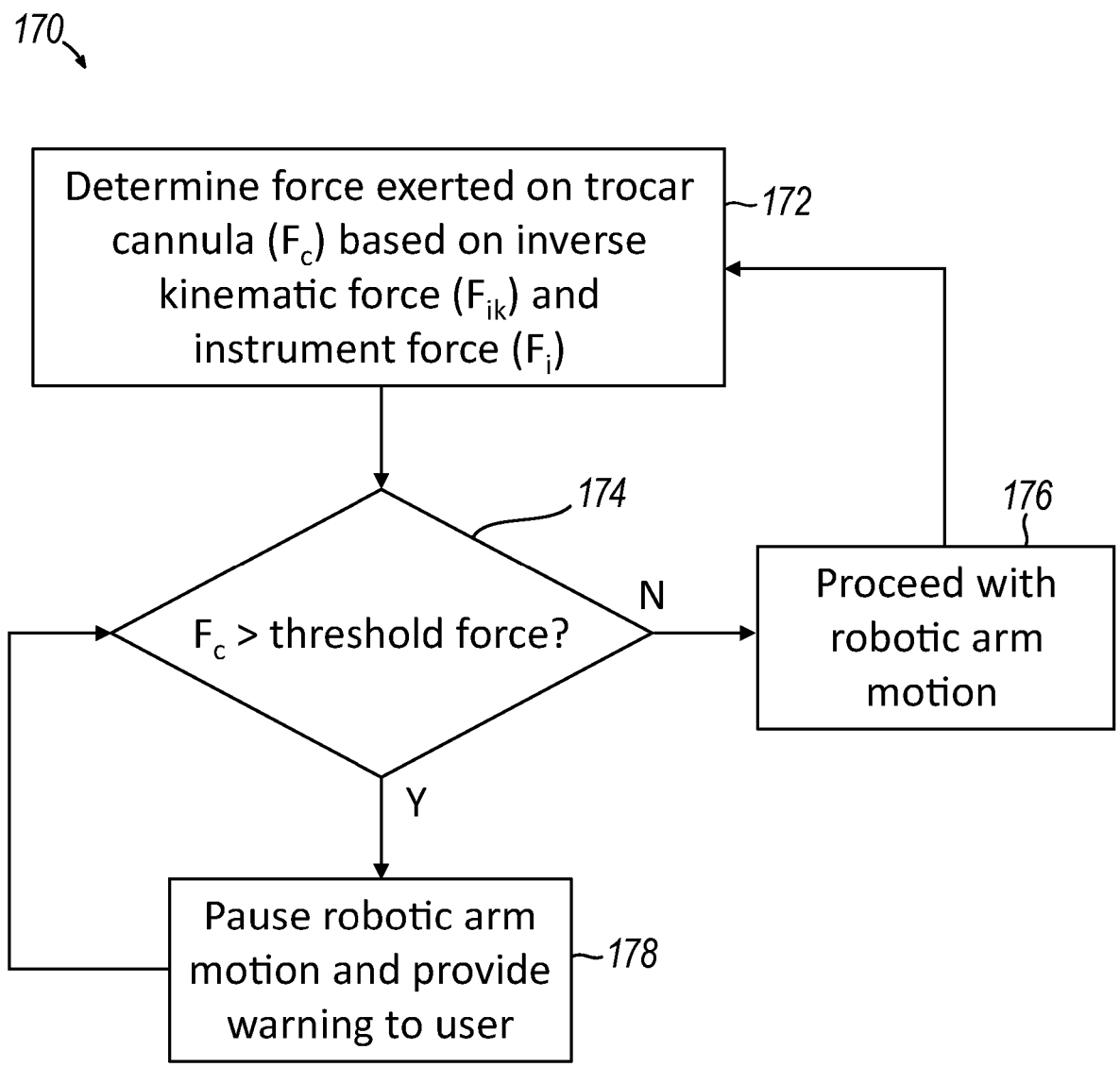
FIG. 11 depicts a diagrammatic view of another exemplary method of manipulating a surgical device relative to a patient using the robotic surgical system of FIG. 1.

FIG. 11 shows an exemplary method (170) of manipulating trocar cannula (100) with robotic arm (160) of robotic surgical system (10) during a surgical procedure based on the determined cannula force ($F_c$) described above. At step (172), control tower (30) determines the cannula force ($F_c$) based on the inverse kinematic force ($F_{ik}$) and the instrument force ($F_i$) acting at that moment. At step (174), control tower (30) assesses whether the cannula force ($F_c$) exceeds a metric in the form of a predetermined threshold force, which may be provided via user input or determined by control tower (30) by accessing one or more databases. In both such scenarios, it will be understood that control tower (30) acknowledges the predetermined threshold force. If no at step (174), control tower (30) proceeds to step (176) and directs robotic arm (160) per the user inputs provided via user console (20). Control tower (30) may then return to step (174) and again assess whether the cannula force ($F_c$) exceeds a predetermined threshold force. Control tower (30) may repeat steps (172) through (176) sequentially throughout the surgical procedure, and if at any point the determined cannula force ($F_c$) exceeds the predetermined threshold force, control tower (30) may interrupt motion of robotic arm (160) at step (178) and optionally provide a warning message to the user via user console (20). In this manner, control tower (30) may ensure that the increased lateral deformation of abdominal wall (W) caused by trocar cannula (100) in a tilted state about a distally position remote center does not rise to the level of exerting an excessive compressive force on the abdominal wall (W) that would otherwise risk trauma to abdominal wall (W).

Figure 12:
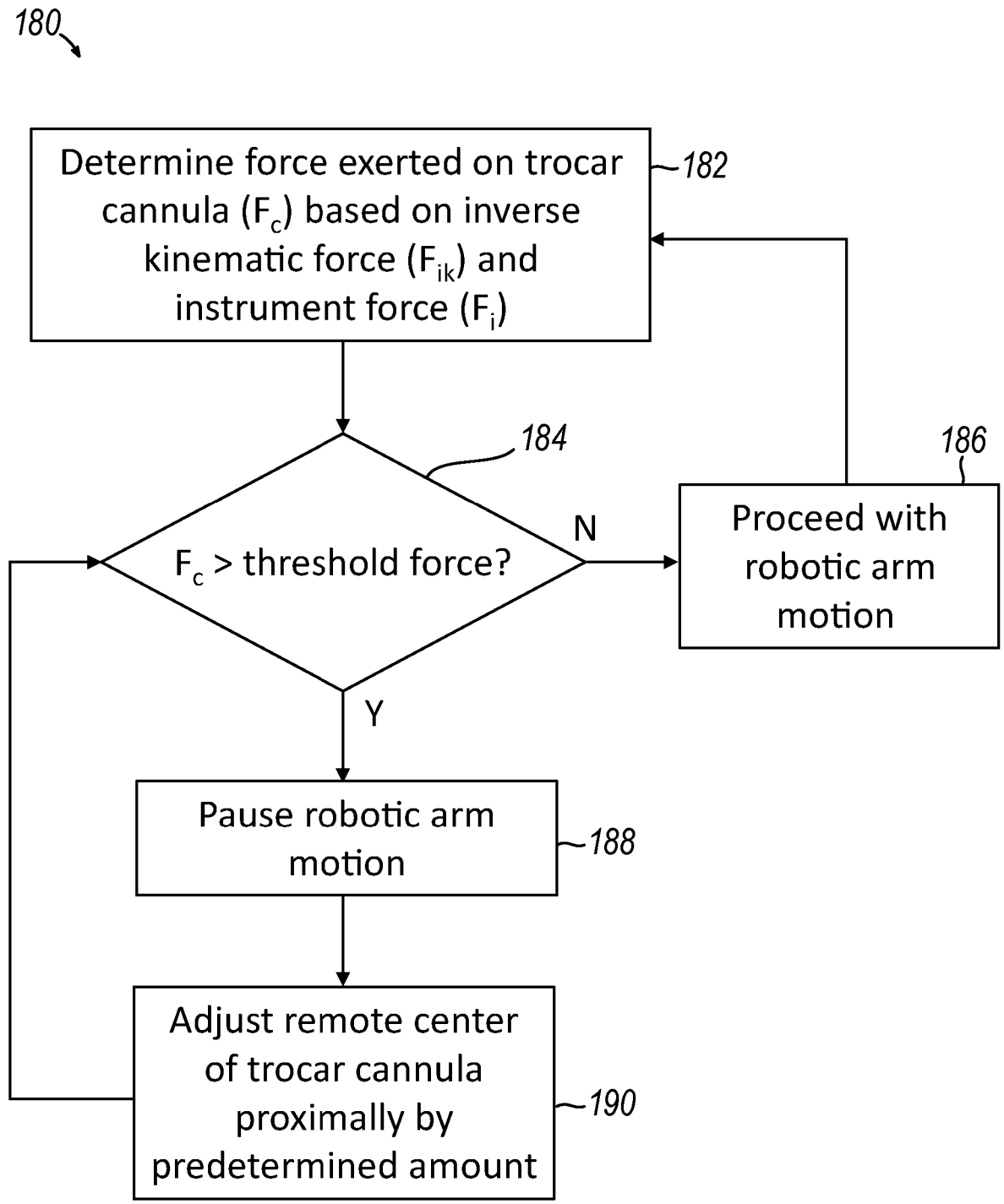
FIG. 12 depicts a diagrammatic view of another exemplary method of manipulating a surgical device relative to a patient using the robotic surgical system of FIG. 1.

FIG. 12 shows another exemplary method (180) of manipulating trocar cannula (100) with robotic arm (160) of robotic surgical system (10) during a surgical procedure based on the determined cannula force ($F_c$) described above. At step (182), control tower (30) determines the cannula force ($F_c$) based on the inverse kinematic force ($F_{ik}$) and the instrument force ($F_i$) acting at that moment. At step (184), control tower (30) assesses whether the cannula force ($F_c$) exceeds a metric in the form of a predetermined threshold force, which may be provided via user input or determined by control tower (30) by accessing one or more databases. If no at step (184), control tower (30) proceeds to step (186) and directs robotic arm (160) per the user inputs provided via user console (20). Control tower (30) may then return to step (184) and again assess whether the cannula force ($F_c$) exceeds a predetermined threshold force. Control tower (30) may repeat steps (184) and (186) sequentially throughout the surgical procedure, and if at any point the determined cannula force ($F_c$) exceeds the predetermined threshold force, control tower (30) may interrupt motion of robotic arm (160) at step (188). Following step (188), control tower (30) proceeds to step (190) and adjusts the remote center of trocar cannula (100) in a proximal direction by a predetermined distance to thereby reduce the lateral deformation of abdominal wall (W) by trocar cannula (100) and thus reduce the cannula force ($F_c$) exerted between trocar cannula (100) and abdominal wall (W). Following step (190), control tower (30) returns to step (184) and reassess whether the determined cannula force ($F_c$) exceeds the predetermined threshold force, and then repeats steps (186) or (188-190) described above as warranted.

Figure 13:
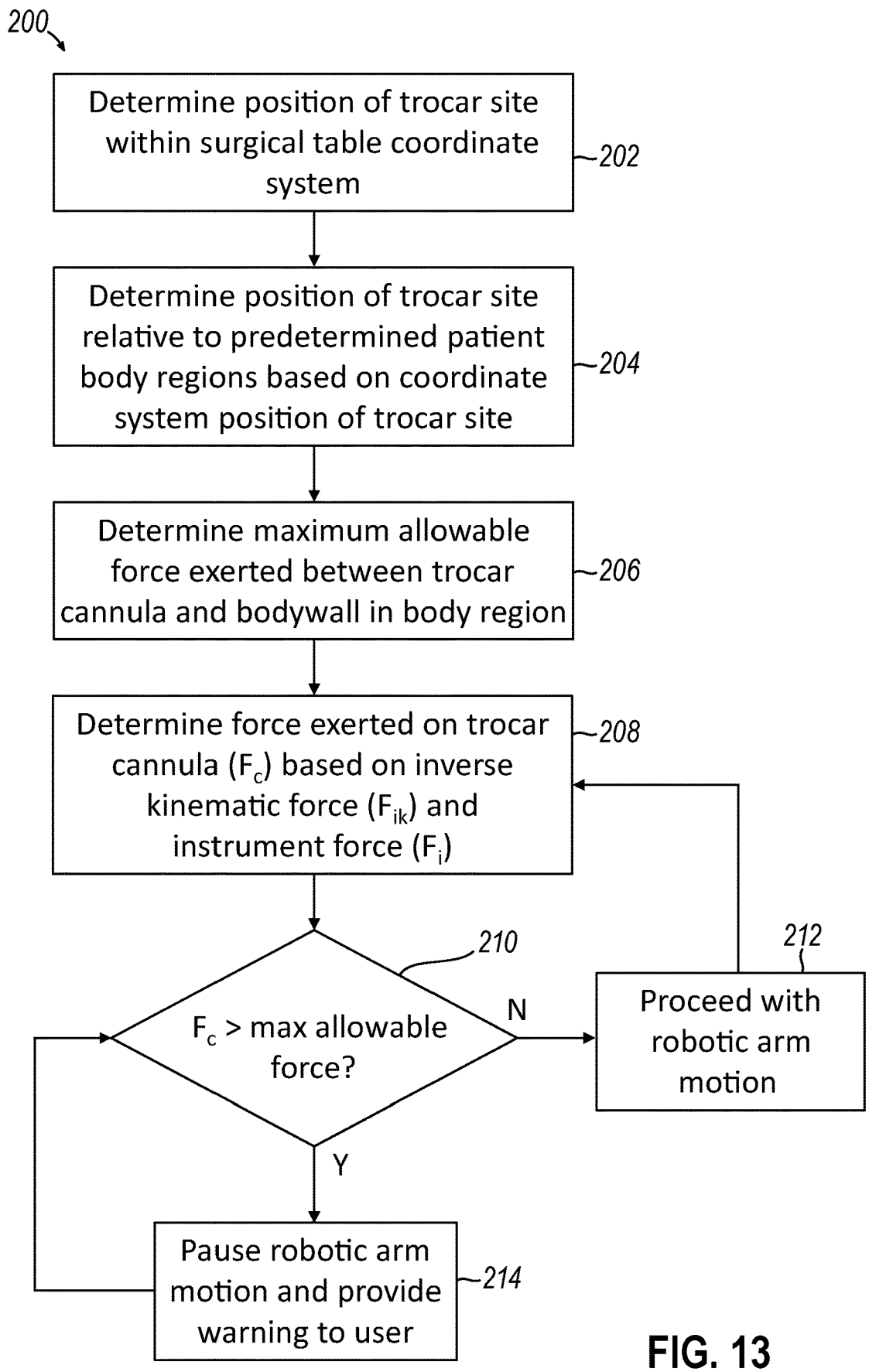
FIG. 13 depicts a diagrammatic view of another exemplary method of manipulating a surgical device relative to a patient using the robotic surgical system of FIG. 1.

FIG. 13 shows yet another exemplary method (200) of manipulating trocar cannula (100) with robotic arm (160) of robotic surgical system (10) during a surgical procedure based on the determined cannula force ($F_c$) described above. A first portion of method (200) is similar to method (140) described above in connection with FIG. 9, and a second portion of method (200) is similar to method (170) described above in connection with FIG. 11. At step (202), control tower (30) determines a position of trocar cannula (100) within an X-Y coordinate system defined by surgical table (T), for example as shown and described above in connection with FIGS. 7-8. Step (202) may be performed based on one or more cameras or other sensors in communication with control tower (30), and/or based on manual input provided by a user via user console (20). At step (204), control tower (30) determines in which body region of patient (P) the determined coordinate system position of trocar cannula (100) is situated. Based on the determination of step (204), control tower (30) at step (206) determines a metric in the form of a maximum allowable force that may be exerted between trocar cannula (100) and abdominal wall (W) so as to avoid undue trauma to abdominal wall (W). Similar to method (140) described above, control tower (30) may perform step (206) by accessing a database that correlates body region with maximum allowable force, where such database is stored locally within control tower (30), or remotely. In some versions, steps (204) and (206) may be performed by control tower (30) as a single step by accessing a database that correlates coordinate system positions of trocar cannula (100) directly with predefined maximum allowable force values.

Still in other versions, control tower (30) may receive user input that specifies the maximum allowable force value, for example via user console (20). In all such versions in which control tower (30) either determines the maximum allowable force value or receives the maximum allowable force value via user input, it will be understood that control tower (30) "acknowledges" the maximum allowable force value, for example in order to perform step (210) described below.

At step (208) of method (200), control tower (30) determines the cannula force ($F_c$) based on the inverse kinematic force ($F_{ik}$) and the instrument force ($F_i$), as described above. At step (210), control tower (30) assesses whether the cannula force ($F_c$) exceeds the maximum allowable force determined in step (206) above. If no, control tower (30) proceeds to step (212) and directs robotic arm (160) per the user inputs provided via user console (20). Control tower (30) may then return to step (208) and again assess whether the cannula force ($F_c$) exceeds the maximum allowable force at step (210). Control tower (30) may repeat steps (208) through (210) sequentially throughout the surgical procedure, and if at any point the determined cannula force ($F_c$) exceeds the maximum allowable force determined in step (206), control tower (30) may interrupt motion of robotic arm (160) at step (214) and optionally provide a warning message to the user via user console (20). Though not shown, in some instances control tower (30) may additionally adjust the remote center of trocar cannula (100) in a proximal direction by a predetermined distance to thereby reduce the lateral deformation of abdominal wall (W) by trocar cannula (100) and thus reduce the cannula force ($F_c$) exerted between trocar cannula (100) and abdominal wall (W).

In an exemplary alternative version of method (200), steps (202, 204) may be omitted. In that regard, control tower (30) may acknowledge a maximum allowable force value, which may be provided via user input for example, without determining a position of trocar cannula (100) relative to patient (P). It will be appreciated that a similar variation of method (140) described above may also be performed.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A robotic surgical system comprising: (a) a robotic arm; (b) a surgical device coupled with the robotic arm, wherein the surgical device is configured to extend through a body wall of a patient; and (c) a controller in communication with the robotic arm, wherein the controller is configured to: (i) determine a position of the surgical device relative to the patient, (ii) acknowledge a maximum allowable metric associated with the body wall at the determined position, (iii) determine a metric associated with the body wall at the determined position, and (iv) drive the robotic arm to manipulate the surgical device such that the determined metric does not exceed the maximum allowable metric.

Example 2

The robotic surgical system of Example 1, wherein the robotic arm includes a distal end to which the surgical device is coupled.

Example 3

The robotic surgical system of any of the preceding Examples, wherein the surgical device comprises a surgical access device having a cannula that is movable relative to the patient, wherein the cannula is configured to receive a surgical instrument therethrough.

Example 4

The robotic surgical system of any of the preceding Examples, wherein the controller is configured to determine a body region of the patient in which the surgical device is positioned.

Example 5

The robotic surgical system of Example 4, wherein the body region includes at least a portion of at least one of a thorax, a margin, an umbilicus, or a pelvis of the patient.

Example 6

The robotic surgical system of any of the preceding Examples, wherein the controller is configured to adjust a remote center of the surgical device relative to the patient.

Example 7

The robotic surgical system of any of the preceding Examples, wherein in response to determining that the determined metric exceeds the maximum allowable metric, the controller is configured to at least one of: (i) pause motion of the robotic arm, (ii) drive the robotic arm to manipulate the surgical device to reduce the determined metric, or (iii) selectively drive the robotic arm to inhibit motion of the robotic arm that would yield a determined metric greater than the maximum allowable metric and simultaneously permit motion of the robotic arm that would yield a determined metric less than or equal to the maximum allowable metric.

Example 8

The robotic surgical system of Example 7, wherein in response to determining that the determined metric exceeds the maximum allowable metric, the controller is further configured to provide a warning to a user of the robotic surgical system.

Example 9

The robotic surgical system of any of Examples 7 through 8, wherein in response to determining that the determined metric exceeds the maximum allowable metric, the controller is further configured to adjust a remote center of the surgical device relative to the patient.

Example 10

The robotic surgical system of Example 9, wherein the controller is configured to adjust the remote center in a direction toward an outer surface of the body wall.

Example 11

The robotic surgical system of Example 1, wherein in acknowledging the maximum allowable metric associated with the body wall at the determined position the controller is configured to at least one of: (A) determine the maximum allowable metric, or (B) receive the maximum allowable metric via user input.

Example 12

The robotic surgical system of any of the preceding Examples, wherein the maximum allowable metric includes at least one of a maximum allowable deformation of the body wall at the determined position or a maximum allowable force exertable between the surgical device and the body wall at the determined position.

Example 13

The robotic surgical system of Example 12, wherein the controller is further configured to: (i) determine a force exerted between the surgical device and the body wall, and (ii) upon determining that the determined force exceeds the maximum allowable force, drive the robotic arm to manipulate the surgical device to reduce the determined force.

Example 14

The robotic surgical system of Example 13, wherein the controller is configured to adjust a remote center of the surgical device relative to the patient.

Example 15

The robotic surgical system of any of Examples 12 through 14, wherein the controller is configured to determine an inverse kinematic force associated with the robotic arm to determine the force exerted between the surgical device and the body wall.

Example 16

A method of manipulating a surgical device relative to a patient with a robotic surgical system having a controller, wherein the surgical device extends through a body wall of the patient, the method comprising: (a) determining with the controller a position of the surgical device within a reference coordinate system; (b) determining with the controller a body region of the patient that corresponds to the determined position; (c) acknowledging with the controller a maximum allowable deformation of the body wall in the determined body region; and (d) manipulating the surgical device with the robotic surgical system such that deformation of the body wall determined by the controller does not exceed the maximum allowable deformation.

Example 17

The method of Example 16, wherein the determined body region comprises at least a portion of an abdomen or a chest of the patient.

Example 18

The method of any of Examples 16 through 17, wherein the robotic surgical system includes a robotic arm and the surgical device is coupled to the robotic arm, wherein the step of manipulating the surgical device with the robotic surgical system includes: (i) manipulating the surgical device with the robotic arm, and (ii) in response to detecting that the determined deformation of the body wall exceeds the maximum allowable deformation, with the controller, at least one of: (A) pausing motion of the robotic arm, or (B) selectively driving the robotic arm to inhibit motion of the robotic arm that would yield a determined deformation greater than the maximum allowable deformation.

Example 19

A method comprising: A method of manipulating a surgical device relative to a patient with a robotic surgical system having a controller, wherein the surgical device extends through a body wall of the patient, the method comprising: (a) determining with the controller a maximum allowable force exertable between the surgical device and the body wall; (b) determining with the controller a force exerted on the surgical device by the body wall; and (c) upon determining that the determined force exceeds the maximum allowable force, with the controller, at least one of: (i) pausing motion of the robotic surgical system, (ii) driving the robotic surgical system to manipulate the surgical device to reduce the observed force, or (iii) selectively driving the robotic surgical system to: (A) inhibit motion of the robotic surgical system that would yield an observed force greater than the maximum allowable force, and (B) permit motion of the robotic surgical system that would yield an observed force less than or equal to the maximum allowable force.

Example 20

The method of Example 19, further comprising, after determining that the determined force exceeds the maximum allowable force, adjusting a remote center of the surgical device relative to the patient in a direction toward an outer surface of the body wall.

Example 21

A method of manipulating a surgical device relative to a patient with a robotic surgical system having a controller, wherein the surgical device extends through a body wall of the patient, the method comprising: (a) determining with the controller a position of the surgical device relative to the patient; (b) determining with the controller a maximum allowable deformation of the body wall at the determined position; (c) determining with the controller deformation of the body wall at the determined position by the surgical device; and (d) manipulating the surgical device with the robotic surgical system such that the determined deformation of the body wall does not exceed the maximum allowable deformation.

Example 22

The method of Example 21, wherein the robotic surgical system includes a robotic arm having an end to which the surgical device is coupled, wherein manipulating the surgical device with the robotic surgical system includes manipulating the surgical device with the robotic arm.

Example 23

The method of any of Examples 21 through 22, wherein the surgical device comprises a surgical access device having a cannula that is movable relative to the patient, wherein the cannula is configured to receive a surgical instrument therethrough.

Example 24

The method of any of Examples 21 through 23, wherein determining the position of the surgical device relative to the patient includes determining a body region of the patient in which the surgical device is positioned.

Example 25

The method of Example 24, wherein the body region includes at least one of a thorax, a margin, an umbilicus, or a pelvis of the patient.

Example 26

The method of any of Examples 21 through 25, wherein manipulating the surgical device with the robotic surgical system includes adjusting a remote center of the surgical device relative to the patient with the controller.

Example 27

The method of any of Examples 21 through 26, further comprising, in response to determining that the determined deformation of the body wall exceeds the maximum allowable deformation, at least one of: (i) pausing motion of the robotic surgical system, or (ii) manipulating the surgical device with the robotic surgical system to reduce the determined deformation of the body wall.

Example 28

The method of Example 27, further comprising, in response to determining that the determined deformation of the body wall exceeds the maximum allowable deformation, providing a warning to a user of the robotic surgical system.

Example 29

The method of any of Examples 27 through 28, further comprising, in response to determining that the determined deformation of the body wall exceeds the maximum allowable deformation, adjusting a remote center of the surgical device relative to the patient with the controller.

Example 30

The method of Example 29, wherein adjusting the remote center of the surgical device with the controller includes adjusting the remote center in a proximal direction.

Example 31

The method of any of Examples 21 through 30, further comprising, after determining the maximum allowable deformation, permitting a user of the robotic surgical system to adjust the maximum allowable deformation.

Example 32

The method of any of Examples 21 through 31, wherein the step of determining with the controller a maximum allowable deformation of the body wall at the determined position includes determining a maximum allowable force exertable between the surgical device and the body wall at the determined position.

Example 33

The method of any Examples 32, further comprising determining with the controller a force exerted on the surgical device by the body wall, wherein manipulating the surgical device with the robotic surgical system includes, upon determining that the determined force exceeds the maximum allowable force, manipulating the surgical device with the robotic surgical system to reduce the determined force.

Example 34

The method of any of Examples 32 through 33, wherein manipulating the surgical device with the robotic surgical system to reduce the determined force includes adjusting a remote center of the surgical device relative to the patient with the controller.

Example 35

The method of any of Examples 32 through 34, wherein the robotic surgical system includes a robotic arm having a free end to which the surgical device is coupled, wherein determining the determined force with the controller includes determining an inverse kinematic force associated with the robotic arm.

Example 36

A method of manipulating a surgical device relative to a patient with a robotic surgical system having an arm, the method comprising: (a) while the surgical device extends through a body wall of the patient, tilting the surgical device with the arm relative to the patient about a first tilt axis that extends through the body wall to position the surgical device in a first orientation relative to the patient; and (b) with the surgical device in the first orientation, tilting the surgical device with the arm relative to the patient about a second tilt axis to position the surgical device in a second orientation relative to the patient, wherein the second tilt axis is offset from the first tilt axis.

Example 37

The method of Example 36, wherein the second tilt axis is proximal or distal to the first tilt axis.

Example 38

The method of any of Examples 36 through 37, wherein the second tilt axis does not extend through the body wall.

Example 39

The method of any of Examples 36 through 38, wherein the second tilt axis is distal to the body wall.

Example 40

The method of any of Examples 21 through 39, wherein the body wall comprises an abdominal wall.

IV. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A robotic surgical system comprising:
   (a) a robotic arm;
   (b) a surgical device coupled with the robotic arm, wherein the surgical device is configured to extend through a body wall of a patient; and
   (c) a controller in communication with the robotic arm, wherein the controller is configured to:
      (i) determine a position of the surgical device relative to the patient,
      (ii) acknowledge a maximum allowable metric associated with the body wall at the determined position, wherein the maximum allowable metric includes a first maximum allowable metric which differs from a second maximum allowable metric associated with the body wall at a second position that is laterally offset from the determined position, wherein the controller is configured to observe a predetermined difference between the first and second maximum allowable metrics based on the determined position of the surgical device and the second position,
      (iii) determine a metric associated with the body wall at the determined position, and
      (iv) drive the robotic arm to manipulate the surgical device such that the determined metric does not exceed the maximum allowable metric.

2. The robotic surgical system of claim 1, wherein the robotic arm includes a distal end to which the surgical device is coupled.

3. The robotic surgical system of claim 1, wherein the surgical device comprises a surgical access device having a cannula that is movable relative to the patient, wherein the cannula is configured to receive a surgical instrument therethrough.

4. The robotic surgical system of claim 1, wherein the controller is configured to determine a body region of the patient in which the surgical device is positioned.

5. The robotic surgical system of claim 4, wherein the body region includes at least a portion of at least one of a thorax, a margin, an umbilicus, or a pelvis of the patient.

6. The robotic surgical system of claim 1, wherein the controller is configured to adjust a remote center of the surgical device relative to the patient.

7. The robotic surgical system of claim 1, wherein in response to determining that the determined metric exceeds the maximum allowable metric, the controller is configured to at least one of:
   pause motion of the robotic arm,
   drive the robotic arm to manipulate the surgical device to reduce the determined metric, or
   selectively drive the robotic arm to inhibit motion of the robotic arm that would yield a determined metric greater than the maximum allowable metric and simultaneously permit motion of the robotic arm that would yield a determined metric less than or equal to the maximum allowable metric.

8. The robotic surgical system of claim 7, wherein in response to determining that the determined metric exceeds the maximum allowable metric, the controller is further configured to provide a warning to a user of the robotic surgical system.

9. The robotic surgical system of claim 7, wherein in response to determining that the determined metric exceeds the maximum allowable metric, the controller is further configured to adjust a remote center of the surgical device relative to the patient.

10. The robotic surgical system of claim 9, wherein the controller is configured to adjust the remote center in a direction toward an outer surface of the body wall.

11. The robotic surgical system of claim 1, wherein in acknowledging the maximum allowable metric associated with the body wall at the determined position the controller is configured to at least one of:
  determine the maximum allowable metric, or
  receive the maximum allowable metric via user input.

12. The robotic surgical system of claim 1, wherein the maximum allowable metric includes at least one of a maximum allowable deformation of the body wall at the determined position or a maximum allowable force exertable between the surgical device and the body wall at the determined position.

13. The robotic surgical system of claim 12, wherein the controller is further configured to:
  determine a force exerted between the surgical device and the body wall, and
  upon determining that the determined force exceeds the maximum allowable force, drive the robotic arm to manipulate the surgical device to reduce the determined force.

14. The robotic surgical system of claim 13, wherein the controller is configured to adjust a remote center of the surgical device relative to the patient.

15. The robotic surgical system of claim 12, wherein the controller is configured to determine an inverse kinematic force associated with the robotic arm to determine the force exerted between the surgical device and the body wall.

16. A method of manipulating a surgical device relative to a patient with a robotic surgical system having a controller, wherein the surgical device extends through a body wall of the patient, the method comprising:
  (a) determining with the controller a device position of the surgical device within a reference coordinate system;
  (b) determining with the controller a first body wall position of the patient that corresponds to the determined device position;
  (c) acknowledging with the controller a first predetermined maximum allowable deformation of the body wall based on the determined first body wall position, wherein the first predetermined maximum allowable deformation of the body wall is different than a second predetermined maximum allowable deformation of the body wall associated with a second body wall position, wherein the first body wall position is laterally offset from the second body wall position; and
  (d) manipulating the surgical device with the robotic surgical system such that deformation of the body wall determined by the controller does not exceed the first predetermined maximum allowable deformation.

17. The method of claim 16, wherein the first body wall position comprises at least a portion of an abdomen or a chest of the patient.

18. The method of claim 16, wherein the robotic surgical system includes a robotic arm and the surgical device is coupled to the robotic arm, wherein the step of manipulating the surgical device with the robotic surgical system includes:
  manipulating the surgical device with the robotic arm, and
  in response to detecting that the determined deformation of the body wall exceeds the first predetermined maximum allowable deformation, with the controller, at least one of:
    pausing motion of the robotic arm, or
    selectively driving the robotic arm to inhibit motion of the robotic arm that would yield a determined deformation greater than the first predetermined maximum allowable deformation.

19. A method of manipulating a surgical device relative to a patient with a robotic surgical system having a controller, wherein the surgical device extends through a body wall of the patient, the method comprising:
  (a) determining with the controller either a first maximum allowable force or a second maximum allowable force exertable between the surgical device and the body wall, wherein the first maximum allowable force is predetermined based on a first position of the surgical device relative to the body wall, wherein the second maximum allowable force is predetermined based on a second position of the surgical device relative to the body wall, wherein the first position and the second position are laterally offset from each other;
  (b) determining with the controller a force exerted on the surgical device by the body wall; and
  (c) upon determining that the determined force exceeds the determined first or second maximum allowable force, with the controller, at least one of:
    (i) pausing motion of the robotic surgical system,
    (ii) driving the robotic surgical system to manipulate the surgical device to reduce the observed force, or
    (iii) selectively driving the robotic surgical system to:
      (A) inhibit motion of the robotic surgical system that would yield an observed force greater than the determined first or second maximum allowable force, and
      (B) permit motion of the robotic surgical system that would yield an observed force less than or equal to the determined first or second maximum allowable force.

20. The method of claim 19, further comprising, after determining that the determined force exceeds the determined first or second maximum allowable force, adjusting a remote center of the surgical device relative to the patient in a direction toward an outer surface of the body wall.

* * * * *